United States Patent [19]
Lee

[11] Patent Number: 5,996,420
[45] Date of Patent: Dec. 7, 1999

[54] MANIFOLD SYSTEMS AND METHODS FOR DELIVERING SAMPLES OF MICROELECTRONIC DEVICE PROCESSING GASES TO GAS ANALYZERS

[75] Inventor: Sok-ho Lee, Kyungki-do, Rep. of Korea

[73] Assignee: Samsung Electronics Co., Ltd., Rep. of Korea

[21] Appl. No.: 09/034,578

[22] Filed: Mar. 4, 1998

[30] Foreign Application Priority Data

Mar. 21, 1997 [KR] Rep. of Korea .................. 97 9876

[51] Int. Cl.[6] .................. G01N 1/00; G01N 30/04
[52] U.S. Cl. .............. 73/764.81; 73/23.41; 73/23.42; 73/863.03
[58] Field of Search .............. 73/863.01, 863.02, 73/863.03, 23.41, 23.42, 864.81; 250/288, 289

[56] References Cited

U.S. PATENT DOCUMENTS

| | | | |
|---|---|---|---|
| 5,209,102 | 5/1993 | Wang et al. | 73/864.81 |
| 5,665,902 | 9/1997 | Wang et al. | 73/864.81 |
| 5,822,951 | 10/1998 | Rosik | 73/863.02 |
| 5,827,945 | 10/1998 | Arnold | 73/23.42 |
| 5,872,306 | 2/1999 | Arnold | 73/23.42 |

*Primary Examiner*—Hezron Williams
*Assistant Examiner*—Chad Soliz
*Attorney, Agent, or Firm*—Myers Bigel Sibley & Sajovec, P.A.

[57] ABSTRACT

Manifold systems and methods for delivering samples of microelectronic device processing gases to gas analyzers include a first passage that receives microelectronic device processing gas from a gas source and discharges the gas at a set pressure through a second passage to a selected gas analyzer. A third passage supplies low-pressure cleaning gas to clean the first and second passages. Multiple gas sources can be connected to multiple gas analyzers via a single manifold system. Steps for distributing semiconductor device processing gas from a gas source to a gas analyzer include purging the first and second passages with low-pressure cleaning gas to remove contaminants. After removing the low-pressure gas from the first and second passages, the first and second passages are isolated from each other and a semiconductor processing gas is discharged from a gas source into the isolated first passage. The semiconductor processing gas is discharged from the first passage to the gas analyzer at a predetermined flow rate and pressure via the second passage. After the semiconductor processing gas has been discharged from the first passage to the gas analyzer, the second passage is isolated from the gas analyzer. Semiconductor processing gas remaining within the first and second passages is then removed. The first and second passages are then purged with high-pressure cleaning gas to remove contaminants.

20 Claims, 2 Drawing Sheets

MANIFOLD SYSTEMS AND METHODS FOR DELIVERING SAMPLES OF MICROELECTRONIC DEVICE PROCESSING GASES TO GAS ANALYZERS

FIELD OF THE INVENTION

The present invention relates generally to microelectronic device manufacturing and, more particularly, to sampling of processing gases used in microelectronic device manufacturing.

BACKGROUND OF THE INVENTION

Generally, microelectronic devices, such as semiconductor devices, are manufactured via a plurality of processing steps, including diffusion, oxidation, photo-lithography, ion implantation, and the like. These processing steps may be performed repeatedly and in a certain order. Each processing step may require a specific processing gas to perform various tasks, such as deposition, etching, purging, and the like. Semiconductor device production yields may be affected by density variations of these processing gases and by contaminants entrained therein. Accordingly, extensive analysis of these processing gases for density variations and contaminants may be performed during the manufacturing of semiconductor devices. Exemplary devices for analyzing processing gases include: Gas Chromatography Discharge Ionic Detector (GC-DIC), Gas Chromatography Thermal Conductivity Detector (GC-TCD); Gas Chromatography Flammable Ionic Detector (GC-FID); Atmospheric Pressure Ionization Mass Spectrometer (API-MS); Electronic Ionization Mass Spectrometer (EI-MS); moisture analyzers, and the like.

Semiconductor processing gases are monitored for density variations and contaminants by analyzing samples thereof. Typically, the supply source of each processing gas has a sample line connected to a corresponding analyzer. Unfortunately, utilizing separate sample lines to supply processing gas samples to multiple analyzers may be somewhat complicated and time consuming, which may lead to lower manufacturing productivity.

SUMMARY OF THE INVENTION

It is therefore an object of the present invention to simplify the delivery of samples of microelectronic device processing gases to analyzers.

It is another object of the present invention to improve microelectronic device manufacturing productivity by improving the handling and analysis of multiple processing gases.

These and other objects of the present invention are provided by a manifold system including a first passage for receiving semiconductor processing gas from a gas source and discharging the gas at a set pressure through a second passage to a selected gas analyzer, and a third passage for supplying low-pressure cleaning gas to clean the first and second passages. A flow control valve may be located within the first passage for controlling the flow of the semiconductor processing gas from the selected gas source into the first passage. A pressure regulator and another flow control valve may be located within the first passage for controlling the pressure and flow rate of the semiconductor processing gas flowing from the first passage to the second passage. The second passage includes separate supply passages to respective gas analyzers. Each respective supply passage may include control valves for directing the flow of semiconductor processing gas into a respective gas analyzer. A third passage in fluid communication with the first passage is configured to supply low-pressure helium for purging the first and second passages of contaminants.

The manifold system also includes a a vacuum pump which serves as means for inducing a vacuum within the first and second passages via a fourth passage. The manifold system further includes a fifth passage configured to supply a high-pressure cleaning gas, such as helium, for purging the first and second passages, for purging the gas source assembly through which a gas source is attached to the first passage, and for detecting leaks within the assembly. In addition, a sixth passage is in fluid communication between the third passage and the fourth passage and facilitates removing contaminants from the third passage when vacuum is induced via the vacuum pump.

According to another aspect of the present invention, steps for distributing semiconductor device processing gas from a gas source to a gas analyzer via a manifold system include: purging the first and second passages with low-pressure cleaning gas to remove contaminants therefrom; removing the low-pressure gas from the first and second passages; isolating the first and second passages from each other; discharging a semiconductor processing gas from a gas source into the isolated first passage up to a predetermined pressure; and discharging the semiconductor processing gas from the first passage to the gas analyzer at a predetermined flow rate and pressure via the second passage. After the semiconductor processing gas has been discharged from the first passage to the gas analyzer, the second passage is isolated from the gas analyzer. Semiconductor processing gas remaining within the first and second passages is then removed. The first and second passages are then purged with high-pressure cleaning gas to remove contaminants therefrom.

The assembly connecting the gas source to the first passage inlet may be purged with a high-pressure cleaning gas to remove contaminants therefrom. The high-pressure cleaning gas may also be used to perform leak detection within the assembly for connecting the gas source with the first passage inlet.

BRIEF DESCRIPTION OF THE DRAWINGS

The accompanying drawings, which are incorporated in and constitute a part of the specification, illustrate an embodiment of the invention and, together with the description, serve to explain the principles of the invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
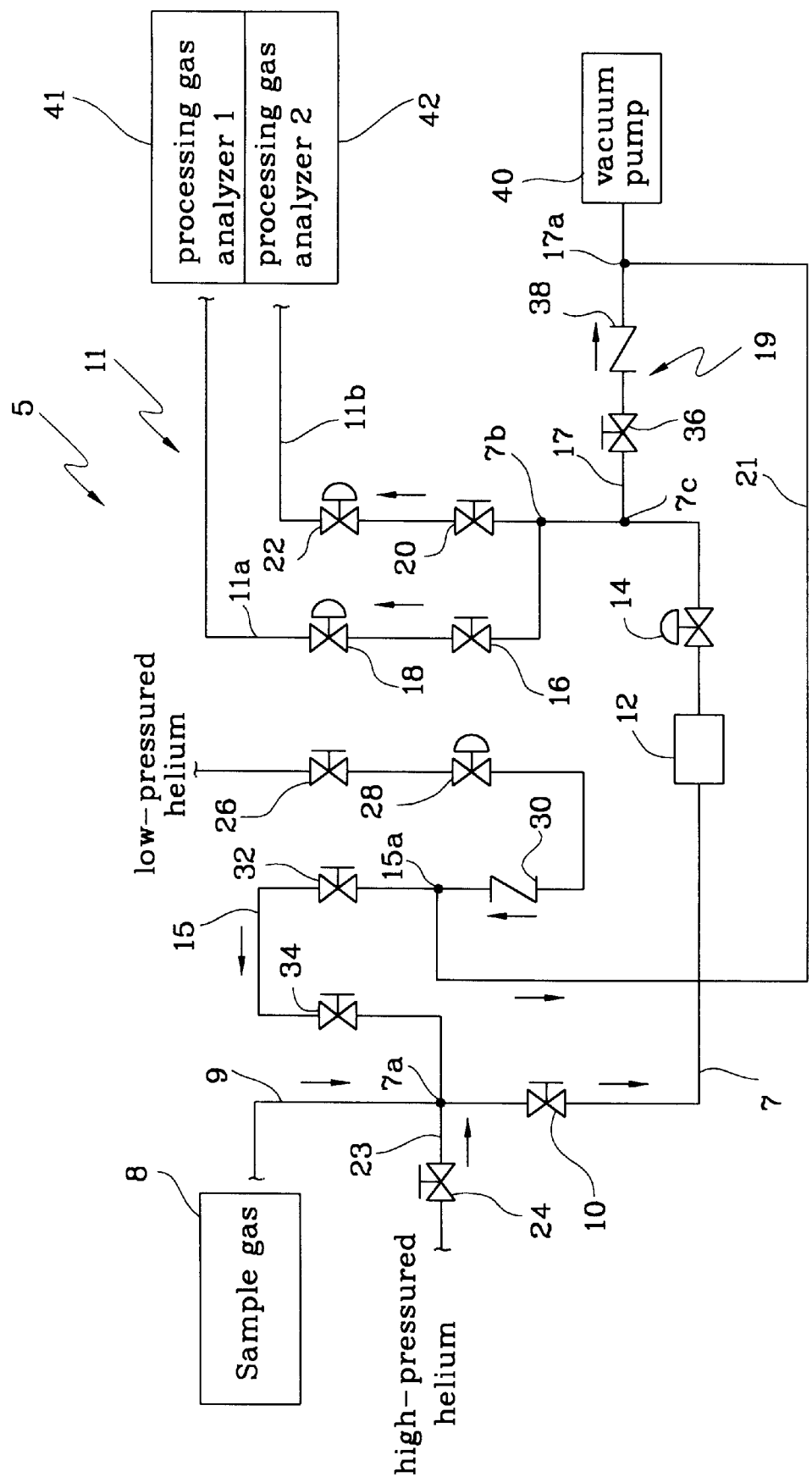
FIG. 1 is a block diagram showing an embodiment of a valve manifold system, according to the present invention.

Referring now to FIG. 1, an embodiment of a manifold system 5 for distributing semiconductor device processing gases from a selected one of a plurality of gas sources to a selected one of a plurality of gas analyzers, according to an embodiment of the present invention, is illustrated. The manifold system 5 includes a first passage 7 having an inlet 7a and an outlet 7b, as illustrated. The first passage inlet 7a is configured to receive pressurized semiconductor processing gas from one or more gas sources (generally indicated as 8). Each gas source 8 is removably connected to an assembly (not shown) which is configured to connect to the first passage inlet 7a via assembly passage 9. The assembly provides a sealed connection with the first passage inlet 7a to permit the semiconductor processing gas to flow into the first passage 7.

The manifold system 5 also includes a second passage 11 in fluid communication with the first passage outlet 7b. The second passage 11 is configured to direct pressurized semiconductor processing gas from the first passage 7 to a selected one of a plurality of gas analyzers. In the illustrated embodiment, the second passage 11 has first and second supply lines 11a, 11b for directing semiconductor processing gas to respective first and second analyzers 41, 42. The first and second supply lines 11a, 11b each have respective flow control valves that serve as means for controlling the flow of semiconductor processing gas from the first passage 7 to a respective gas analyzer 41, 42. In the illustrated embodiment, supply line 11a includes valves 16, 18. Preferably, valve 16 is a bellows-type valve, and valve 18 is an on/off-type valve. Supply line 11b includes valves 20, 22. Preferably, valve 20 is a bellows-type valve, and valve 22 is an on/off-type valve. Valves 16 and 20 reduce sudden impacts of semiconductor processing gas under pressure caused by the sudden opening of valves 18 and 22, respectively, when flow control valve 14 in the first passage 7 is open.

The first semiconductor processing gas analyzer 41 is preferably used to analyze a specific gas provided from a specific gas source 8 in fluid communication with the first passage 7. The second semiconductor processing gas analyzer 42 is preferably used to analyze a different gas provided from a different gas source in fluid communication with the first passage 7. Accordingly, the manifold system 5 is capable of directing multiple different semiconductor processing gases to multiple respective gas analyzers.

It is to be understood that the present invention is not limited to two semiconductor processing gas analyzers, as illustrated. Various numbers and configurations of semiconductor processing gas analyzers may be utilized with the manifold system 5, without limitation. Preferably, the second passage 11 will include additional supply lines and flow control valves for each additional gas analyzer. In addition, the manifold system 5 of the present invention may be utilized with various analyzers including, but not limited to, GC-DID, GC-TCD, GC-FID, API-MS, EI-MS, and humidity analyzers.

The first passage 7 includes a flow control valve 10 which serves as means for controlling the flow of a semiconductor processing gas into the first passage from a selected gas source 8. The first passage 7 also includes a pressure regulator 12 located downstream from the flow control valve 10. The pressure regulator 12 serves as means for controlling the pressure of a semiconductor processing gas flowing from the first passage 7 to the second passage 11. Another flow control valve 14 is located downstream from the pressure regulator 12 and serves as means for controlling the flow rate of a semiconductor processing gas flowing from the first passage to the second passage.

The manifold system 5 also includes a third passage 15 in fluid communication with the first passage inlet 7a. The third passage 15 is configured to supply a low pressure cleaning gas, such as helium, for purging the first and second passages. The third passage 15 contains valves 26, 28, 30, 32 and 34 installed in sequence as illustrated. The valves contained within the third passage 15 serve as means for controlling the flow rate of the low pressure cleaning gas into the first and second passages 7, 11. As is described below, low pressure cleaning gas, such as helium, is used to purge the first and second passages 7, 11 of contaminants and remaining semiconductor processing gas.

The manifold system 5 also includes a a vacuum pump 40 which serves as means for inducing a vacuum within the first and second passages 7, 11 via a fourth passage 17, as illustrated. The fourth passage 17 is a vacuum line in fluid communication with the first passage 7 downstream from the second flow control valve 14. In the illustrated embodiment, the fourth passage 17 connects with the first passage 7 at the location indicated as 7c. The fourth passage 17 includes valves 36, 38, as illustrated, which serve as vacuum control means 19 for controlling vacuum induced within the first and second passages 7, 11.

The manifold system 5 further includes a fifth passage 23 in fluid communication with the first passage inlet 7a. As is described below, the fifth passage is configured to supply a high pressure cleaning gas, such as helium, for purging the first and second passages 7, 11, for purging the gas source assembly through which a gas source 8 is attached to the first passage inlet 7a, and for detecting leaks within the assembly.

In addition, a sixth passage 21 is in fluid communication between the third passage 15 and the fourth passage 17 downstream of valves 30 and 38, respectively. In the illustrated embodiment, the sixth passage 21 connects with the third passage 15 at 15a and connects with the fourth passage 17 at 17a. The sixth passage facilitates removing contaminants from the third passage 15 when vacuum is induced via the vacuum pump 40.

The inner walls of the passages of the manifold system 5 are preferably electrically polished and have durability against explosive and/or corrosive gases. In addition, it is preferred that valves 14, 18, 22, and 28 are on/off-type valves, and that the remaining non-check valves are bellows-type valves.

Figure 2:
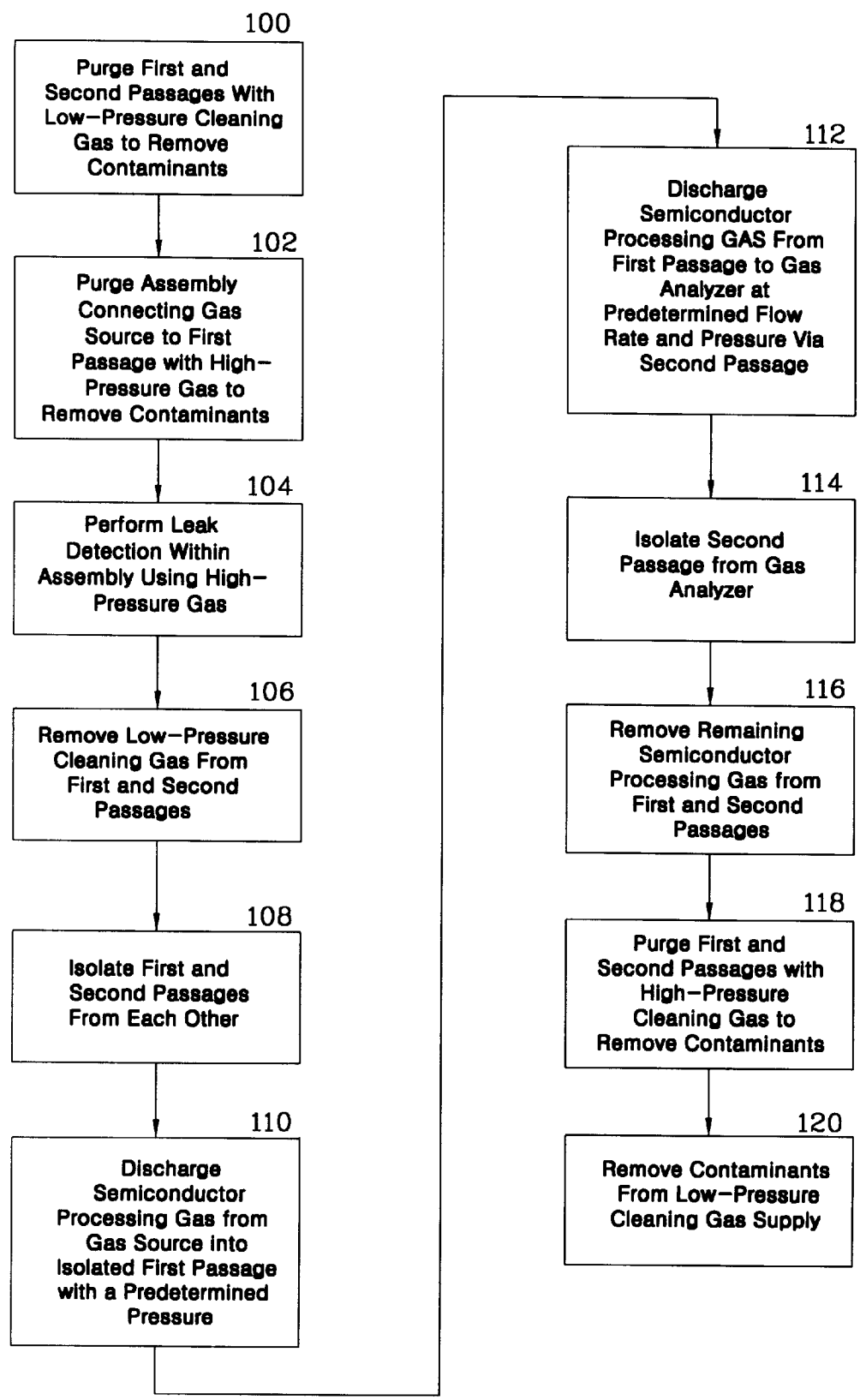
FIG. 2 is a flow diagram schematically illustrating steps for distributing semiconductor processing gas from a gas source to a gas analyzer via a manifold system according to the present invention.

Referring now to FIG. 2, operations for distributing semiconductor device processing gas from a gas source to a gas analyzer via a manifold system according to the present invention are schematically illustrated. Prior to the induction of a semiconductor processing gas into the manifold system for subsequent analysis in a gas analyzer, the first and second passages (7 and 11, FIG. 1) are purged with a low-pressure cleaning gas, such as helium, to remove contaminants therefrom (Block 100). The assembly connecting the gas source to the first passage inlet is purged with a high-pressure cleaning gas to remove contaminants therefrom (Block 102). The high-pressure cleaning gas may also be used to perform leak detection within the assembly for connecting the gas source with the first passage inlet (Block 104).

The low-pressure cleaning gas is then removed from the first and second passages (Block 106), and the first and second passages are isolated from each other (Block 108). A semiconductor processing gas to be analyzed by a gas analyzer is discharged from the gas source into the isolated first passage up to a predetermined pressure (Block 110). The semiconductor processing gas under pressure within the first passage is then discharged from the first passage to the gas analyzer at a predetermined flow rate and pressure via the second passage (Block 112). After the semiconductor processing gas has been discharged from the first passage to the gas analyzer, the second passage is isolated from the gas analyzer (Block 114). Semiconductor processing gas remaining within the first and second passages is then removed (Block 116). The first and second passages are then purged with high-pressure cleaning gas to remove contaminants therefrom (Block 118). Contaminants are then removed from the low-pressure cleaning gas supply (Block 120).

Operations for distributing semiconductor processing gas to gas analyzers using the manifold system 5 illustrated in FIG. 1 will now be explained. If it is desired that a sample of semiconductor processing gas be analyzed via the second gas analyzer 42, the high-pressure helium valve 24 is closed. Low-pressure helium is induced into the first and second passages 7, 11 by opening valves 26, 28, 32, 34 and 10. The pressure regulator 12 and valves 14, 20 and 22 are also maintained in an open position. By contrast, if the first gas analyzer were to be used, valves 16 and 18 would be open and valves 20 and 22 would remain closed.

The first and second passages 7, 11 of the manifold system 5 are constantly purged with low pressure helium until an assembly for supplying a semiconductor processing gas for analysis is set up. Before an assembly for supplying a semiconductor processing gas is installed on the first passage inlet 7a, valves 10 and 34 are closed and high pressure helium is induced into the assembly passage 9. This allows the high pressure helium to be discharged into the connection area of the assembly to the first passage inlet 7a, and thereby remove any remaining contaminants present between valves 10 and 34, and between the valve 10 and the connection site of the assembly.

In addition, leaks in the assembly and the connection with the first passage inlet 7a can be detected using high-pressure helium supplied through valve 24. Preferably, leak detection is performed to protect against the risk of fire or explosion caused by leakage of explosive or toxic gas.

Valve 24 is then closed after leak detection operations. Helium is present in the first and second passages 7, 11. Valve 10 is then closed and helium present between valve 10 and the specific processing gas analyzer is removed by opening valve 36 and allowing the vacuum pump 40 to induce a vacuum within the first and second passages 7, 11. The helium discharge conditions are checked via the pressure regulator 12. Preferably, a pressure gauge is installed on the pressure regulator 12 for monitoring the pressure.

After helium has been removed from the manifold, valve 10 is opened and a sample of semiconductor processing gas is induced into the first passage 7 up to the end of the pressure regulator 12. The semiconductor processing gas is induced into the first passage 7 with a certain pressure depending on the specific purpose of the processing gas analyzer. For example, a humidity analyzer may require the semiconductor processing gas to be supplied for up to a maximum of twenty minutes. The amount of the gas needed to satisfy the twenty minute duration is calculated and the pressure that the gas is to be delivered to the gas analyzer is set in the pressure regulator 12. The first passage 7 is charged with the semiconductor processing gas up to the desired pressure level and then valve 10 is closed.

The sample of semiconductor processing gas within the first passage 7 is supplied into a specific processing gas analyzer at a pressure controlled by the pressure regulator 12. For example, semiconductor processing gas is supplied to the second processing gas analyzer 42 by opening valve 14, closing valves 16 and 18, and opening valves 20 and 22. The pressure regulator 12 maintains an appropriate sample gas pressure. The analysis for the supplied semiconductor processing gas is then carried out in the second processing gas analyzer 42.

After the analysis of the supplied semiconductor processing gas for contaminants is completed in the second processing gas analyzer 42, valves 32, 28, 26, 20, and 22 are closed. Then, the remaining semiconductor processing gas is pumped out of the first and second passages 7, 11 through open valve 36 via the vacuum pump 40. The purge is carried out with valves 10, 28, 30, 16, and 20 closed.

The vacuum pump 40 preferably stops after pumping for a certain time. Valve 36 is then closed, and high-pressure helium gas is induced through valve 24 to remove microcontaminants present inside the first and second passages 7, 11.

Then, valves 24 and 20 are closed slowly so as to discharge out the remaining gas. After the complete discharge of the remaining gas, valve 10 is closed, and with valve 24 open, the gas source assembly is removed and the end of the assembly passage 9 is sealed with a cap.

After sealing the path end with a cap, the above-described supply of low-pressure helium gas starts again, and the flow of the low-pressure helium gas cleans the inside of the first and second passages 7, 11 until the analysis of the next sample of semiconductor processing gas is carried out.

At least one of the following processing gas analyzers can be connected to embodiments of the present invention: GC-DID, GC-FID, GC-TCD, API-MS, EIMS, or humidity analyzer. The present invention allows a sample of semiconductor processing gas to be supplied to a processing gas analyzer such that it is not necessary to readjust the processing gas analyzer according to its purpose. The sample of semiconductor processing gas to be analyzed can be controlled by controlling the supply time and valve opening/closing operations. Accordingly, preparation time for gas analysis can be reduced.

By using a manifold system, according to the present invention, sample analysis efficiency can be increased. By increasing analysis efficiency, gas that is sufficient in both quantity and quality can be supplied to various semiconductor device manufacturing operations. In addition, an embodiment of the present invention anticipates a Random Monitoring System for monitoring various gas samples. It is to be understood that the present invention may be utilized in conjunction with manufacturing operations for various microelectronic devices, and is not limited to semiconductor devices.

As a result, according to the present invention, processing gas for semiconductor device manufacturing can be supplied in compliance with the characteristics of various processing gas analyzers maximizing its analysis capability. In addition, the easy supply of sample gas for the analysis of almost all kinds of gas improves the efficiency of the system application. Further, the sufficient amount of the supplied gas also improves the productivity of the semiconductor devices.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A manifold system that distributes microelectronic device processing gas from a selected one of a plurality of gas sources to a selected one of a plurality of gas analyzers, said manifold system comprising:
    a first passage having an inlet and an outlet, said inlet configured to receive pressurized microelectronic device processing gas from said selected gas source;
    a second passage in fluid communication with said first passage outlet and configured to direct pressurized microelectronic device processing gas from said first passage to said selected gas analyzer;
    first means for controlling flow of said microelectronic device processing gas from said selected gas source into said first passage, said first means located within said first passage;
    pressure control means, located within said first passage, downstream from said first flow control means, for controlling pressure of said microelectronic device processing gas flowing from said first passage to said second passage;
    second means for controlling flow rate of said microelectronic device processing gas flowing from said first passage to said second passage, said second means located within said first passage downstream from said pressure control means;
    third means for controlling flow of said microelectronic device processing gas from said first passage to said selected gas analyzer, said third means located within said second passage; and
    a third passage in fluid communication with said first passage inlet and configured to supply a first cleaning gas at a first pressure to purge said first and second passages.

2. A manifold system according to claim 1 further comprising means for inducing vacuum within said first and second passages via a fourth passage in fluid communication with said first passage downstream from said second flow control means.

3. A manifold system according to claim 2 wherein said fourth passage comprises means for controlling vacuum induced within said first and second passages.

4. A manifold system according to claim 1 further comprising a fifth passage in fluid communication with said first passage inlet and configured to supply a second cleaning gas having a second pressure for purging said first and second passages.

5. A manifold system according to claim 1 wherein said second passage comprises a plurality of supply lines, each of said plurality of supply lines in fluid communication with a respective gas analyzer.

6. A manifold system according to claim 5 wherein each of said plurality of supply lines comprises flow control means for controlling flow of a microelectronic device processing gas from said first passage to a respective gas analyzer.

7. A manifold system according to claim 1 wherein said third passage comprises fourth means for controlling flow rate of said first cleaning gas into said first and second passages.

8. A manifold system according to claim 3 further comprising a sixth passage in fluid communication between said third passage and said fourth passage downstream of said vacuum control means, said sixth passage facilitating removal of contaminants from said third passage when vacuum is induced via said vacuum inducing means.

9. A method of distributing microelectronic device processing gas from a gas source to a gas analyzer via a manifold, the manifold comprising a first passage configured to receive microelectronic device processing gas from the gas source, wherein the first passage has an inlet and an outlet, and a second passage in fluid communication with the first passage outlet and configured to direct the microelectronic device processing gas from the first passage to the gas analyzer, said method comprising the steps of:
    purging the first and second passages with a first cleaning gas having a first pressure to remove contaminants therefrom;
    removing the first cleaning gas from the first and second passages;
    isolating the first and second passages after the first cleaning gas has been removed from the first and second passages;
    discharging microelectronic device processing gas from the gas source into the isolated first passage up to a predetermined pressure; and
    discharging the microelectronic device processing gas from the first passage to the gas analyzer at a predetermined flow rate and pressure via the second passage.

10. A method according to claim 9 further comprising the step of purging an assembly for connecting the gas source with the first passage inlet using a second gas having a second pressure to thereby remove contaminants therefrom prior to said step of discharging the microelectronic device processing gas from the first passage to the gas analyzer.

11. A method according to claim 10 further comprising the step of using the second cleaning gas to perform leak detection within the assembly for connecting the gas source with the first passage inlet prior to said step of discharging the microelectronic device processing gas from the first passage to the gas analyzer.

12. A method according to claim 10 further comprising the following steps after said step of discharging the microelectronic device processing gas from the first passage to the gas analyzer:
    isolating the second passage from the gas analyzer;
    removing from the first and second passages any microelectronic device processing gas remaining therein; and
    purging the first and second passages with the second cleaning gas having a second pressure to remove contaminants therefrom.

13. A method according to claim 10 wherein the first and second cleaning gases comprise helium.

14. A method according to claim 10 wherein the first pressure is lower than the second pressure.

15. A method according to claim 9 wherein the first cleaning gas is provided via a third passage in fluid communication with the first passage.

16. A method according to claim 15 further comprising the step of removing contaminants from a portion of the third passage after said step of discharging the microelectronic device processing gas from the first passage to the gas analyzer via the second passage.

17. A method according to claim 9 wherein said step of removing the first cleaning gas from the first and second passages is performed by inducing a vacuum in the first and second passages via a fourth passage in fluid communication with the first passage.

18. A method according to claim 16 wherein said step of removing contaminants from a portion of the third passage is performed by inducing a vacuum in a portion of the third passage via a sixth passage in fluid communication with the third and fourth passages.

19. A method of distributing microelectronic device processing gas from a selected one of a plurality of gas sources to a selected one of a plurality of gas analyzers via a manifold, the manifold comprising a first passage configured to receive processing gas from the selected gas source via an assembly passage, and a second passage in fluid communication with the first passage and configured to direct the microelectronic device processing gas from the first passage to the selected gas analyzer, the method comprising the steps of:

purging the first and second passages with a first helium gas having a first pressure to remove contaminants therefrom, wherein the first helium gas is provided via a third passage in fluid communication with the first passage;

removing the first helium gas from the first and second passages by inducing a vacuum in the first and second passages via a fourth passage in fluid communication with the first passage;

isolating the first and second passages after the first helium gas has been removed from the first and second passages;

discharging microelectronic device processing gas from the selected gas source into the isolated first passage up to a predetermined pressure;

discharging the microelectronic device processing gas from the first passage to the selected gas analyzer at a predetermined flow rate and pressure via the second passage;

isolating the second passage from the selected gas analyzer after the microelectronic device processing gas has been discharged to the selected gas analyzer;

removing from the first and second passages any microelectronic device processing gas remaining therein; and purging the first and second passages with a second cleaning gas having a second pressure to remove contaminants therefrom.

20. A method according to claim 19 further comprising the step of purging the assembly passage with a second helium gas having a second pressure higher than the first pressure of the first helium gas to remove contaminants therefrom prior to said step of discharging the pressurized processing gas from the first passage to the first gas analyzer.

* * * * *

UNITED STATES PATENT AND TRADEMARK OFFICE
CERTIFICATE OF CORRECTION

PATENT NO. : 5,996,420

DATED : December 7, 1999

INVENTOR(S) : Sok-ho Lee

It is certified that error appears in the above-identified patent and that said Letters Patent is hereby corrected as shown below:

Title page, item [56],
In References Cited please add:

-- 5,281,397; 5,487,313; 5,652,398 and 5,711,786--

Signed and Sealed this

Sixth Day of February, 2001

Attest:

Q. TODD DICKINSON

*Attesting Officer*　　　　*Director of Patents and Trademarks*